United States Patent
Matsunaka et al.

[11] Patent Number: 5,305,098
[45] Date of Patent: Apr. 19, 1994

[54] ENDOSCOPE IMAGE PROCESSING SYSTEM WITH MEANS FOR DISCRIMINATING BETWEEN ENDOSCOPE IMAGE AREA AND CHARACTER IMAGE AREA

[75] Inventors: Kenji Matsunaka; Yoshitaka Miyoshi, both of Hachioji, Japan

[73] Assignee: Olympus Optical Co., Ltd., Tokyo, Japan

[21] Appl. No.: 865,872

[22] Filed: Apr. 9, 1992

[30] Foreign Application Priority Data

Apr. 11, 1991 [JP] Japan ................. 3-078982
Mar. 9, 1992 [JP] Japan ................. 4-050859

[51] Int. Cl.[5] .................. A61B 1/04; H04N 7/18
[52] U.S. Cl. .................. 348/65; 358/403; 358/462; 348/45
[58] Field of Search ........ 358/98, 403, 462, 88; H04N 7/18

[56] References Cited

U.S. PATENT DOCUMENTS

| 4,819,065 | 4/1989 | Eino | 358/98 |
| 5,111,306 | 5/1992 | Kanno | 358/403 |
| 5,124,789 | 6/1992 | Hiyama | 358/403 |
| 5,196,928 | 3/1993 | Karasawa | 358/98 |

Primary Examiner—Howard W. Britton
Attorney, Agent, or Firm—Armstrong, Westerman, Hattori, McLeland & Naughton

[57] ABSTRACT

A video signal generator produces a video signal which contains an endoscope image sensed by an image sensor and a character image comprising an ID code, etc. The video signal generator is connected to an image processing unit via a communication circuit, through which information indicating an arrangement for respective signal areas of the endoscope image and the character image contained in the video signal is transmitted. Based on the information received by the communication circuit, the image processing unit performs different processing for each image area of the endoscope image and the character image contained in the video signal.

25 Claims, 17 Drawing Sheets

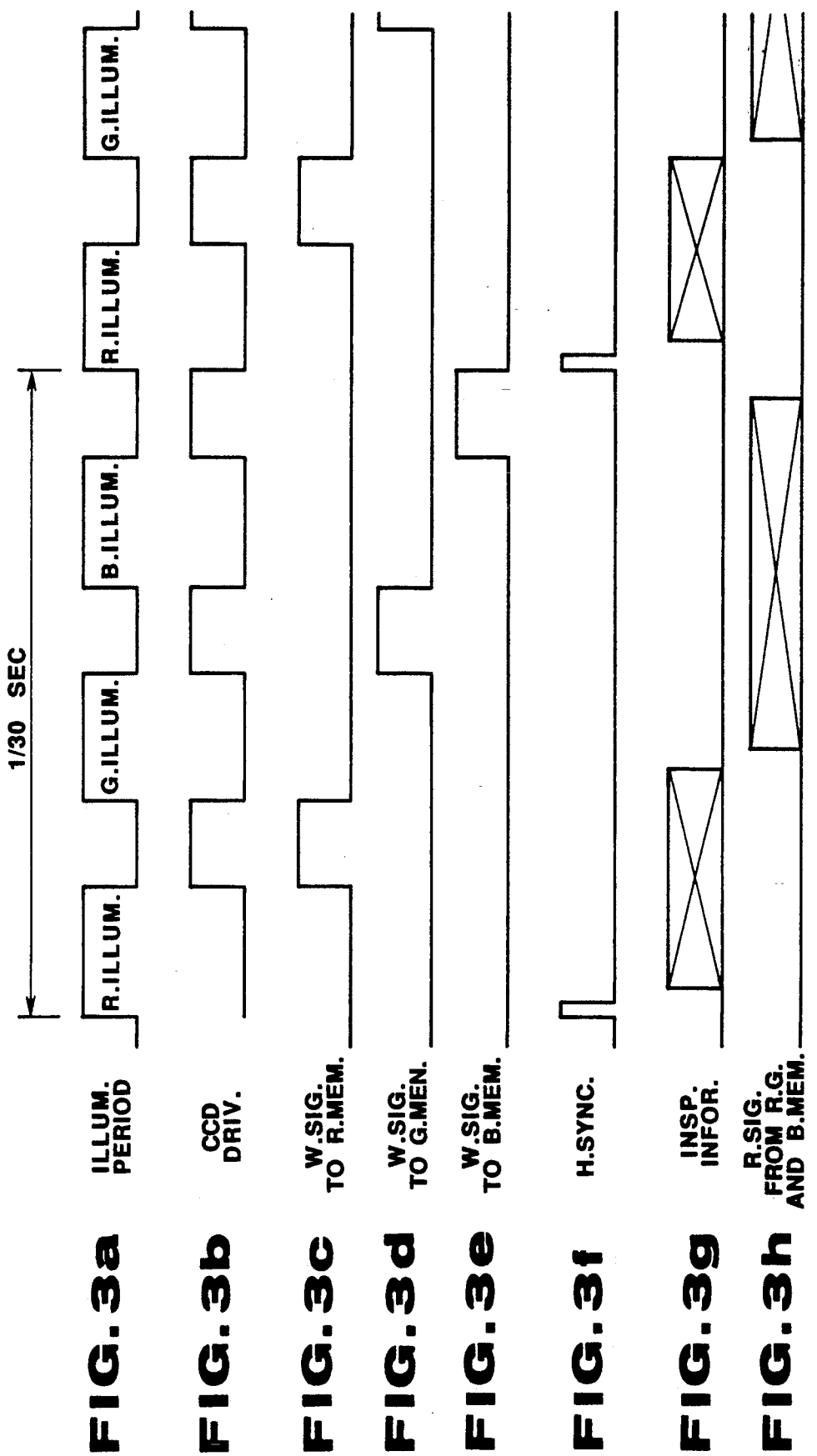

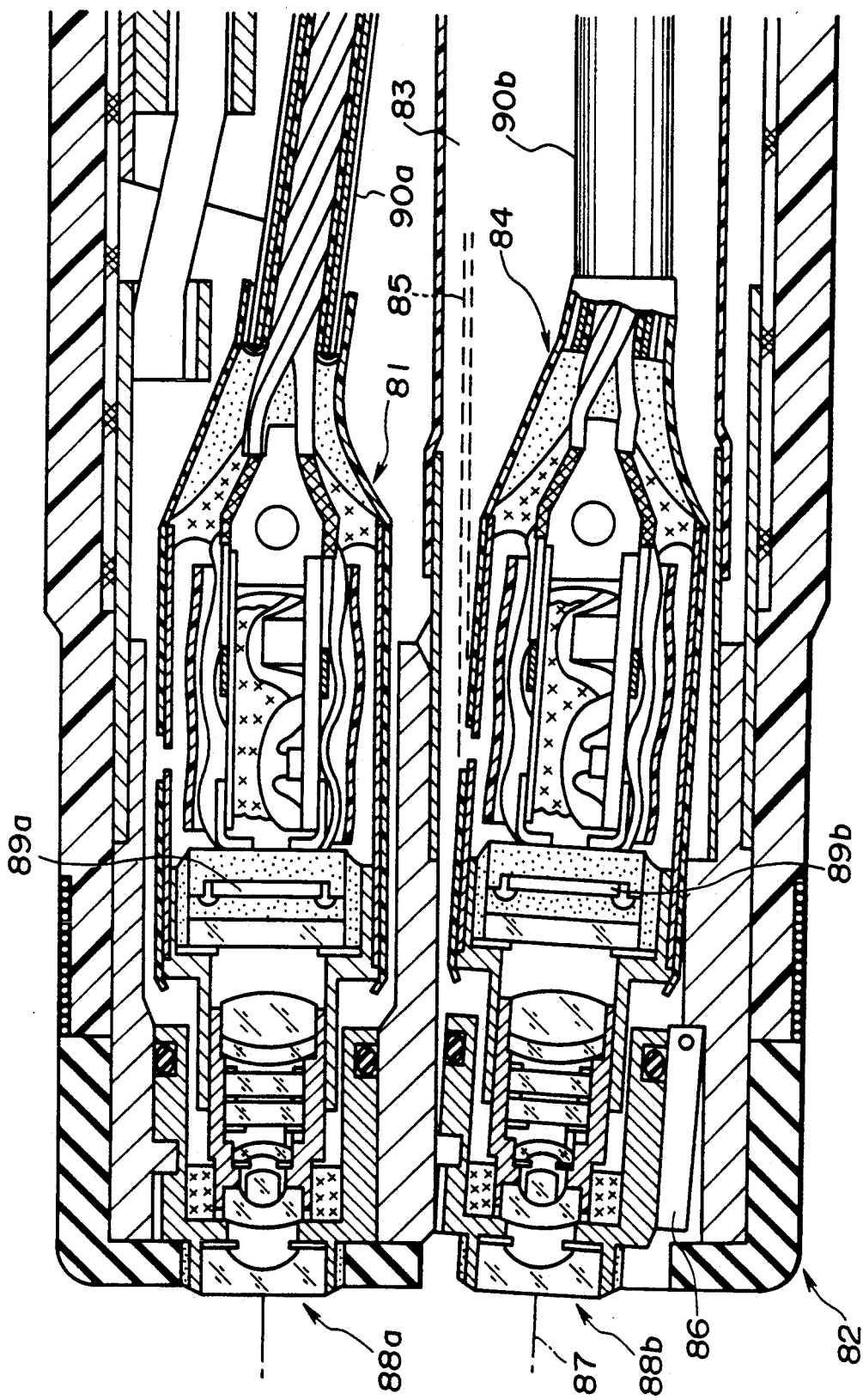

ENDOSCOPE IMAGE PROCESSING SYSTEM WITH MEANS FOR DISCRIMINATING BETWEEN ENDOSCOPE IMAGE AREA AND CHARACTER IMAGE AREA

BACKGROUND OF THE INVENTION

Field of the Invention and Description of the Related Art

The present invention relates to an endoscope image processing system that even when an endoscope image area and a character image area to be displayed on a monitor using video signals are changed, image processing can be performed in such a manner as adapted for each area.

Recently, there have been widely employed endoscopes (referred to also as scopes or fiber scopes) which enable an operator to observe body organs or the like by inserting an elongate insert section into the body cavity, and also to perform various medical treatments by using appliances inserted through an appliance channel at need.

Various types of electronic scopes having image sensing means, which comprises a solid state image sensor such as a charge coupled device (abbreviated as CCD) and are built therein, are also used. These electronic scopes have such advantages as a higher degree of resolution than fiber scopes, easy recording and reproduction of images, as well as easy image processing including enlargement of images and comparison of two image screens, for example. In view of the above, there is further employed an apparatus of the type that a TV camera is mounted at an eyepiece of a fiber scope to realize nearly comparable functions to those of an electronic scope (the apparatus being referred to as TV camera integrated scopes).

An endoscope image outputted for visual display from image sensing means of an electronics type scope given by the above electronic scope or TV camera integrated scope is converted into a video signal added with character information such as letters (or a character image) for indicating information needed to identify the endoscope image, the video signal being recorded in a large capacity recording device such as a hard disk unit or magneto-optical disk unit.

Because the number of pixels used in the image sensing means of the electronics type scope is less than resolution with which a monitor can display and the display screen of a monitor is horizontally long in general cases, an area where no endoscope image is displayed occurs at the end of the image screen in the horizontal direction. Usually, a video signal containing an endoscope image and character information added thereto is created so as to display letter information in such an area where no endoscope image is displayed.

A method of recording the video signal containing an endoscope image and character information added thereto is mainly divided into analog type and digital type. The digital type method is superior to the analog type method in a point of maintaining image quality. When recording data by the digital type method, however, since an extremely large amount of data must be handled, it is usual to carry out processing called coding compression, followed by storing the reduced amount of data in a recording device.

In an attempt to perform the coding compression, there occurs a considerable difference in the time required for calculations and the data amount after calculations between the case of compressing one pixel as a multi-value image like a color image represented by 24 bits, for example, and the case of compressing one pixel as a two-value image like a monochromatic image (or character information) represented by 1 bit. When using the digital type method to record image information for a screen in which a colored endoscope image is present only in a particular area and monochromatic letters are displayed in the remaining area, like a monitor screen of an endoscope device, it is therefore effective to divide the entire screen area into twos and process data in different manners of compression corresponding to the respective areas.

One easily conceivable method for division into two areas is practiced by specifying the construction of an input screen in advance at the side of an image processing unit and dividing the screen into a multi-value (three or more-value) image area and a two-value image area in accordance with the specifications. Another conceivable method is effected by an operator who designates a way of division into two areas through area designating means, as disclosed in Japanese Patent Laid-Open No. 2-112378.

With the former method of specifying the construction of an input screen, however, some of endoscope devices display a color image in a larger area than others. This implies that when the image processing unit sets the boundary between a color area and a monochromatic area, the boundary must be set in match with the maximum area for a color image available among a variety of endoscope devices.

Accordingly, the former method suffers from a disadvantage of requiring longer time for compression calculations and data transfer than necessary and increasing an amount of data in the case where such images of endoscope deices as having a small color image area, i.e., a small endoscope area, in the screen.

On the other hand, the latter method of dividing the screen into two areas by the area designating means has a problem of enlarging a burden imposed on the operator because a mouse, tablet or the like is required as the area designating means and the operator has to carefully input each image area.

OBJECT AND SUMMARY OF THE INVENTION

An object of the present invention is to provide an endoscope image processing system that even when display areas of endoscope images are different from each other depending on endoscopes, image processing can be automatically performed in a suitable manner corresponding to the current display area.

Another object of the present invention is to provide an endoscope image processing system that an image having been subjected image processing can be obtained in a shorter period of time even for those endoscope images having display areas different from each other.

The endoscope image processing system of the present invention comprises:

an endoscope having an image sensor, a video signal generator for generating a video signal which contains an endoscope image created through signal processing for the image sensor and a character image relating to the endoscope image, information generating means provided in the video signal generator for automatically generating information corresponding to an area arrangement for respective signal areas of the endoscope image and the character image in the video signal, an image processing unit for carrying out image processing of the video signal, and communication means provided between the video signal generator and the image processing unit for transmitting the information to the image processing unit, whereby the image processing unit can discriminate the two image areas based on the information transmitted through the transmission means. Accordingly, even when the endoscope image becomes different in size as experienced in the case of using another image sensor which has the different number of pixels, the image processing unit can properly discriminate the area of the endoscope image and perform image processing of the endoscope image portion in an suitable manner different from that for the character image.

BRIEF DESCRIPTION OF THE DRAWINGS

FIGS. 1 to 9 are concerned with a first embodiment of the present invention in which:

FIG. 1 is a perspective view of an endoscope image file system equipped with the first embodiment;

FIG. 2 is a view showing construction of an endoscope device in the first embodiment;

FIG. 3 is a set of timing charts for explaining operation of the endoscope device of FIG. 2;

FIG. 4 is a set of diagrams for explaining display examples on a monitor;

FIG. 5 is a block diagram showing arrangement of an image file controller in the first embodiment;

FIG. 6 is a block diagram showing arrangement of an image processing section which constitutes the image file controller;

FIG. 7 is a block diagram showing arrangement of main parts according to a first modification of the first embodiment;

FIG. 8 is a block diagram showing arrangement of main parts according to a second modification of the first embodiment; and FIG. 9 is a set of charts showing waveforms when transmitting image arrangement information in synchronism with a video signal.

FIGS. 10 and 11 are concerned with a second embodiment of the present invention in which:

FIG. 10 is a view showing construction of an endoscope device in the second embodiment; and FIG. 11 is a set of timing charts for explaining operation of the endoscope device of FIG. 10.

FIGS. 12 to 20 are concerned with a third embodiment of the present invention in which:

FIG. 12 is a view showing entire construction of a stereo type endoscope device;

FIG. 13 is a view for explaining construction of the distal end portion of the stereo type endoscope device;

FIG. 14 is a block diagram showing arrangement of a light source unit, a signal processing unit, etc. in FIG. 12;

FIG. 15 is a block diagram showing arrangement of an image processing unit in FIG. 14;

FIG. 16 is a set of views for explaining 2-bit discrimination signals corresponding to screen compositions;

FIG. 17 is a flowchart showing a typical example of inspection (or examination) in the image processing unit;

FIG. 18 is a set of explanatory views showing display examples on a monitor screen;

FIG. 19 is a set of explanatory views showing behavior as produced when the distance between an endoscope distal end and an observed location is changed; and FIG. 20 is a sectional view of a stereo type endoscope realized by inserting image sensing units into respective channels in an electronic endoscope.

DETAILED DESCRIPTION OF THE PREFERRED EMBODIMENTS

Figure 1:
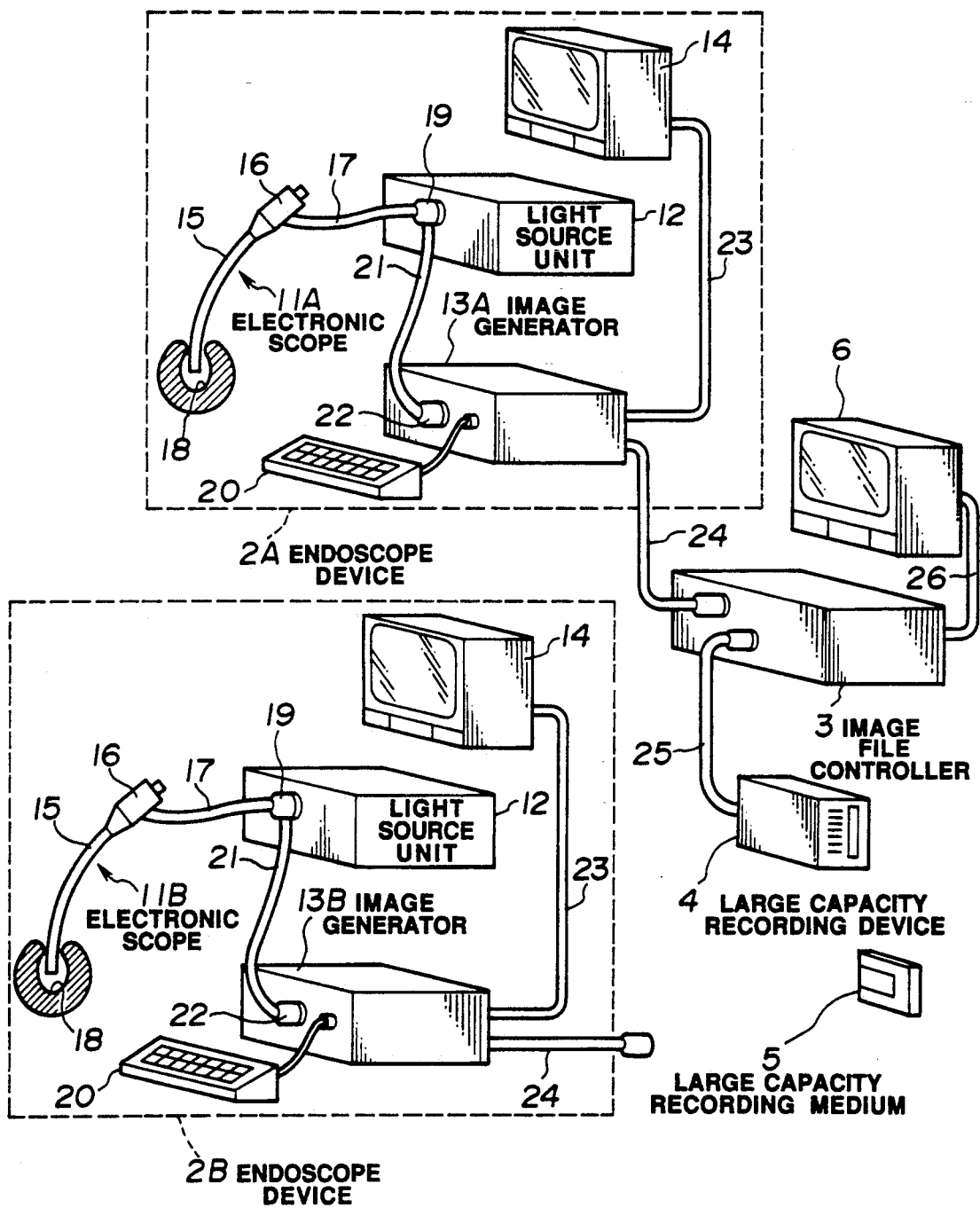

As shown in FIG. 1, an endoscope image file system 1 comprises an endoscope device 2A equipped with means for generating an image signal, an image file controller 3 equipped with means for carrying out image processing, a large capacity recording device 4 for recording an image, etc. having been subjected to the image processing and reproducing the recorded image, a large capacity recording medium 5 associated with the large capacity recording device 4 to perform recording/reproduction of data, and a TV monitor 6 for displaying a video signal outputted from the image file controller 3. As an alternative, the endoscope image file system 1 may be constituted by connecting another endoscope device 2B, which employs a CCD different in the number of pixels from the endoscope device 2A, to the image file controller 3.

As shown in FIG. 1, the endoscope device 2I (I=A or B) comprises an electronic scope 11I with image sensing means built therein, a light source unit 12 for supplying an illumination light to the electronic scope 11I, an image generator 13I for carrying out signal processing, etc. related to the electronic scope 11I and outputting the video signal, and a TV monitor 14 for displaying the video signal outputted from the image generator 13I.

The electronic scope 11I includes an insert section 15 which is elongate and flexible, an operating section 16 joined to the rear end of the insert section 15, and a universal cable 17 extending from the side of the operating section 16. By inserting the insert section 15 into the body cavity or the like, an operator can observe a location 18 in the body cavity to be observed. The universal cable 17 is provided at its end with a connector 19 which can be connected to the light source unit 12 for supplying the illumination light to the electronic scope 11.

A signal cable 21 is extending from the side of the connector 19 and a connector 22 provided at the end of the cable 21 can be connected to the image generator 13.

The image generator 13I is connected to a keyboard 20 through which inspection (or examination) information such as patient data is inputted, and also processes an image signal obtained from the electronic scope 11I to produce the video signal, such as a set of RGB signals of three primary colors, for superimposing the inspection information on the video signal and displaying the same on a display screen of the TV monitor 14 via a cable 23 along with an endoscope image. The resulted display permits the operator to make endoscopic observation.

The image generator 13I can also send, to the image file controller 3, device discriminating information that determines screen composition (image construction) information consisted of the endoscope image and the inspection information.

Further, the image generator 13I allows input means in the form of the keyboard 20 to send data and a control signal to the image file controller 3, thereby providing instruction and control for recording or retrieval of images, etc. with respect to the large capacity recording device 4 connected to the image file controller 3.

The video signal produced by the image generator 13I, as well as the data and the control signal are sent to the image file controller 3 via the cable 24. In the image file controller 3, the video signal and the inspection information are converted into digital data and processed through data compression, etc. into coded data which is then sent to the large capacity recording device 4 via the cable 24. The large capacity recording device 4 records the coded data on the large capacity recording medium 5 of portable type. The image file controller 3 also extends the compressed data to display a reproduced image on the TV monitor 6 via a cable 26, allowing the operator to observe the reproduced image.

Arrangement of the endoscope device 2A will now be described with reference to FIG. 2. A light guide 27 in the form of a fiber bundle is inserted through the insert section 15 and the universal cable 17 of the electronic scope 11A, so that the illumination light is supplied to the light guide 27 by connecting the connector 19 to the light source unit 12. Thus, a white light emitted from a lamp 12c enters a rotating filter 12b which is driven by a motor 12a to rotate.

Attached to the rotating filter 12b are sector-shaped color filters 12R, 12G, 12B through which lights in wavelength ranges of red, green and blue are transmittable, such that the color filters 12R, 12G, 12B sequentially pass a position facing a lamp 12c. Accordingly, the white light irradiated to the rotating filter 12b are converted by the color filters 12R, 12G, 12B into lights in wavelength ranges of red, green and blue, i.e., frame-sequential lights, following which those lights are condensed by a condenser lens 12d and irradiated to one end face of the light guide 27. Furthermore, the motor 12a is controlled in its rotational speed by a motor drive 12e so as to rotate at the constant timing of 30 r.p.s., for example. As shown in FIG. 3a, therefore, three illumination periods of red, green and blue occur for 1/30 sec.

The above frame-sequential lights are transmitted through the light guide 27 and emitted forwardly from the other end face of the light guide 27 which is fixed to an illumination window at the distal end of the insert section 15, thereby illuminating the location 18 to be observed. An image of the location 18 to be observed is focused by an object lens 29, fixed to an observation window at the distal end of the insert section 15, on a CCD 30A arranged in the focal plane of the object lens 29.

An optical image focused by the object lens 29 is subjected to photoelectric conversion in the CCD 30A. A CCD drive signal is applied from a CCD driver 13a in the image generator 13 to the CCD 30A during each of light interruption periods in FIG. 3a, whereupon the signal photoelectrically converted in the CCD 30A is read and inputted to an amplifier 13b in the image generator 13A for amplification.

The signal amplified by the amplifier 13b is subjected to signal processing, such as $\gamma$ correction, in a process circuit 13c and, thereafter, each pixel signal from the CCD 30A is converted by an A/D converter 13d into a digital signal of 8 bits, for example, the digital signal being temporarily stored in R, G and B memories 43R, 43G, 43B via a switch 13e.

The switch 13e is changed over by a switching signal from a controller 13f at the constant timing of 1/90 sec, for example, so that the digital signal converted by the A/D converter 13d is sequentially stored in the R, G and B memories 43R, 43G, 43B.

Respective signals produced from the illumination lights of red, green and blue and sensed during the illumination periods of red, green and blue are, as shown in FIGS. 3c, 3d and 3e, are stored in the R, G and B memories 43R, 43G, 43B upon a write signal applied thereto, respectively. The R, G and B memories 43R, 43G, 43B each have memory cells in larger number than the number of pixels of the CCD 30A, and each memory cell has a storage capacity equal to at least the number of bits necessary for the A/D conversion in the A/D converter 13d.

The image signal data stored in the R, G and B memories 43R, 43G, 43B are simultaneously read on the basis of a vertical synch signal (not shown) and a horizontal synch signal as shown in FIG. 3f at the constant timing of 1/30 sec, for example. As shown in FIG. 3b, those data are read out of the R, G and B memories 43R, 43G, 43B at the same time after a predetermined period of time from the horizontal synch signal under control of the controller 13f. The vertical synch signal and the horizontal synch signal are outputted from a synch signal generator 13m shown in FIG. 2.

The image signal data simultaneously read out of the R, G and B memories 43R, 43G, 43B are converted into analog color signals R, G, B in a D/A converter 13g having a D/A converting function of 8 bits, for example. After being masked in peripheral edges of each image by a masking circuit (not shown), the analog color signals are outputted via mixers 12h, 12i, 12j to the side of the monitor 14 and the image file controller 3 for displaying the image of the location sensed by the CCD 30A to be observed, i.e., the endoscope image. Display examples of such an endoscope image section are shown in FIG. 4.

The horizontal and vertical synch signals S outputted from the synch signal generator 13m are also outputted to the side of the monitor 14 and the image file controller 3 along with the color signals R, G, B.

The controller 13f is connected to the keyboard 20 via a keyboard interface 13n, and inspection information such as an ID code, name, sex and comment for identifying the patient corresponding to the endoscope image can be entered by key operation of the keyboard 20. Upon the key operation, the controller 13f reads out corresponding characters via a character generator 13p and temporarily stores them in an inspection) information storage memory 13r.

The inspection information stored in the memory 13r is outputted to the side of the monitor 14 and the image file controller 3 via the mixers 12h, 12i, 12j. The memory 13r has memory cells in number enough to indicate the inspection information, comprising character information, at an arbitrary position on the display screen of the monitor 14. Also, the memory 13r has a capacity for storing data of 1-bit code notation.

More specifically, because the endoscope image is in the form of analog signals and it is desirable to reduce errors in quantization caused during conversion into the digital signals, the image data is converted using code notation of 8 bits, for example. On the other hand, because the inspection information is in the form of character information such as letters and each pixel (or a signal corresponding to each pixel) is represented by 1-bit data, i.e., white or black, it is sufficient that each memory cell of the memory 13r for storing each pixel has a capacity of 1 bit.

The inspection information is outputted as shown in FIG. 3g. Thus, the inspection information is outputted during a period between the horizontal synch signal shown in FIG. 3f and the endoscope image shown in FIG. 3h.

Figure 2:
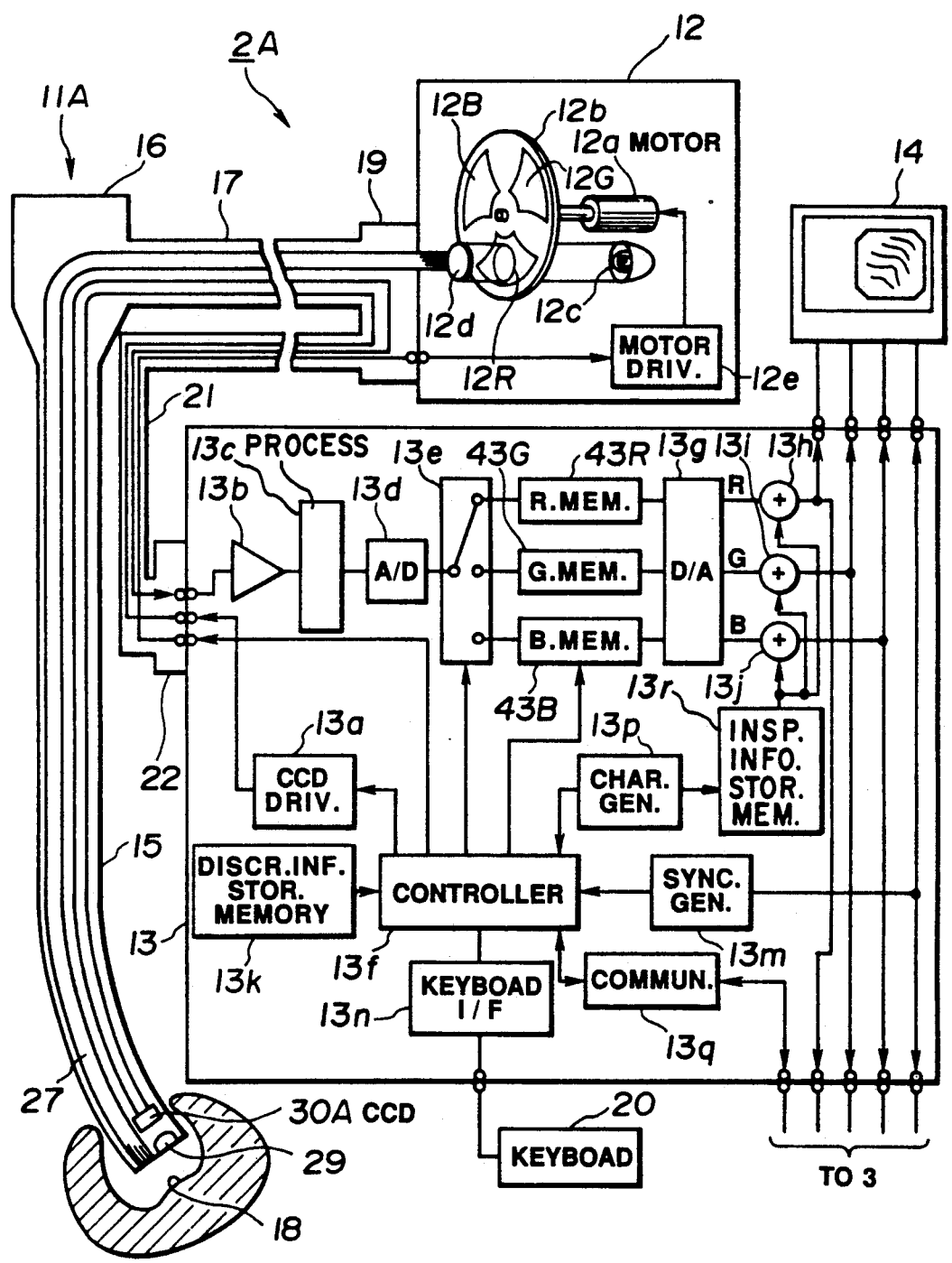
Figure 4A:
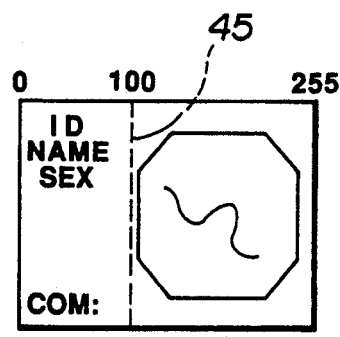

In the endoscope device 2A of FIG. 2, by way of example, the image screen of the monitor 14 is arranged to display the inspection information on the left side of the endoscope image as shown in FIG. 4a. Meanwhile, in the case of another system where an endoscope device using a CCD different in the number of pixels, etc. from the CCD 30A shown in FIG. 2 is connected to the image file controller 3, a screen example as shown in FIG. 4b or 4c is displayed on the monitor 14.

Figure 4B:
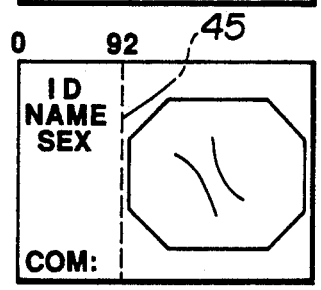
Figure 4C:
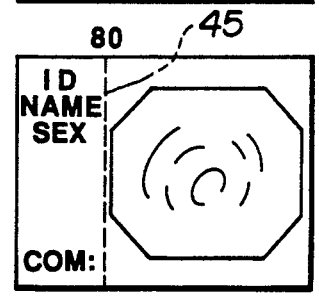

As will be seen from FIGS. 4a, 4b and 4c, the endoscope image and the inspection information are separately displayed on the right and left of a vertical line 45 indicating the boundary at which the respective screen composing areas are divided. The horizontal position of the vertical line 45, indicating that boundary, is expressed by, for example, any value of 8 bits, i.e., any one of 0 to 255.

The position of the line 45 is different for each type of the endoscope devices 2I using the CCD 30I which are different in the number of pixels and so forth, and it corresponds to the device discriminating information (in one to one relation) associated with each of different types endoscope devices. The device discriminating information is stored in an discriminating information storage memory 13k within the image generator 13I and transmitted to the image file controller 3 from the controller 13f via a communication circuit 13q.

Additionally, the operator can transmit a control signal and/or data to the image file controller 3 by operating the keyboard 20. It is possible to, by way of example, send via the image file controller 3 control signals for recording, reproduction and retrieval of the large capacity recording device 4, and/or data necessary in the retrieval process.

The controller 13f sends a control signal to the motor driver 12e for synchronous execution of signal processing in the image generator 13 and rotation of the rotating filter 12b.

Figure 5:
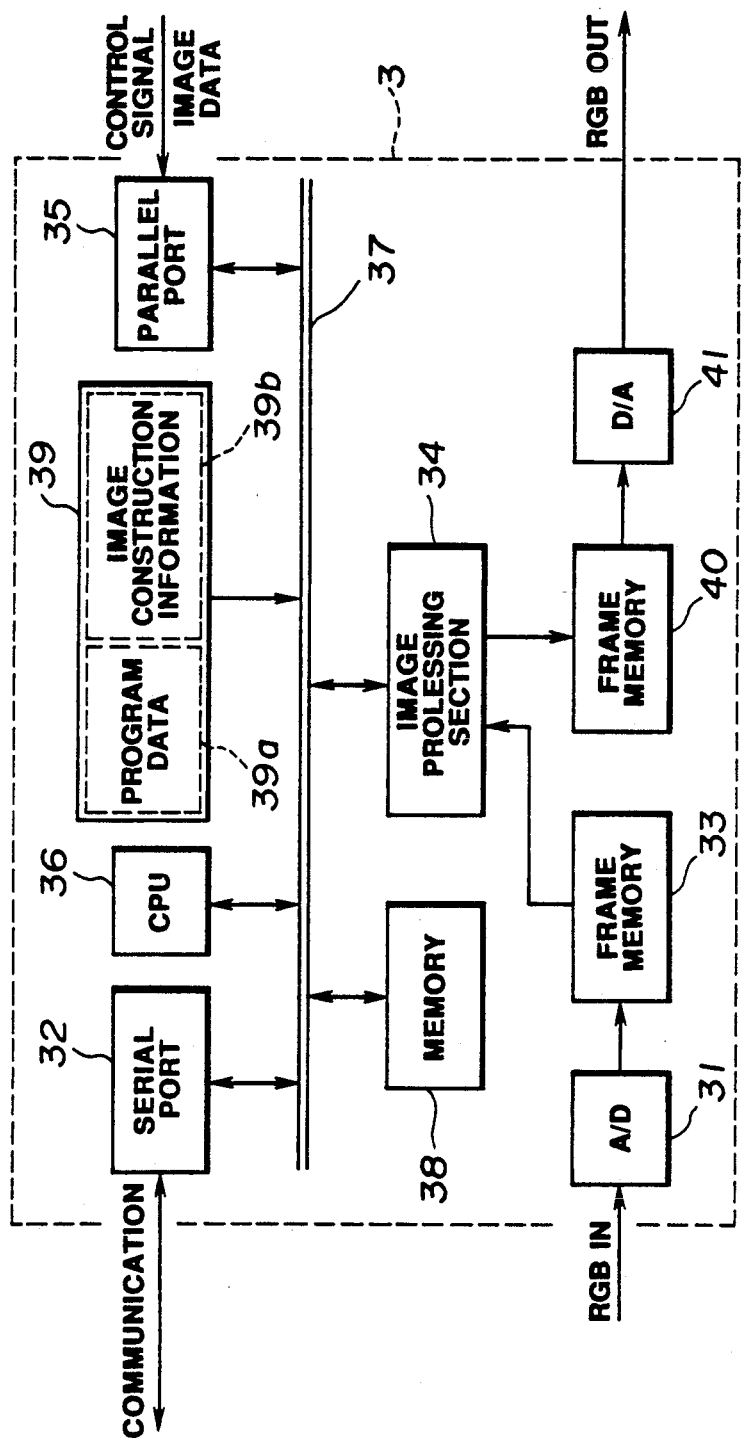

Internal arrangement of the image file controller 3 will be next described with reference to FIG. 5. The video signal RGB and the synch signal S from the image generator 13A are inputted to an A/D converter 31 for conversion into digital signals. On the other hand, the data and the control signal from the image generator 13A are inputted to and outputted from a serial port 35 via the cable 24.

The image data converted into the digital signal by the A/D converter 31 is temporarily stored in a first frame memory 33 and then sent to an image processing section 34. The large capacity recording device 4 is able to input and output the coded data of the image and the control signal with respect to the parallel port 35. A CPU 36 is able to input and output the data and the control signal with respect to a serial port 32, the parallel port 35, a memory 38, the image processing section 34 and a ROM 39 through a bus line 37.

The ROM 39 stores therein program data 39a to be executed by the CPU 36 and a set of screen composition (image construction) information 39b for the various endoscope devices 2. In an image display mode, the image processing section 34 extends the compressed coded data and transfers the same to a second frame memory 40, following which a D/A converter 41 produces a video signal of RGB to display an image on the TV monitor 6.

In this embodiment, the image generator 13I is able to send the device discriminating information for the endoscope device 2I to the serial port 32 of the image file controller 3 via the cable 24. Upon the device discriminating information being inputted via the serial port 32, the image file controller 3 discriminates the type of the endoscope device 2I based on the device discriminating information and transfers the information of screen composition depending on the discriminated type among the set of screen composition information 39b in the ROM 39. When the image information to be indicated on the display screen is expressed by the size ranging from 0 to 255 in the horizontal direction, as shown in FIGS. 4a to 4c, the screen composition information stands for that the screen consists of an area ranging from 0 to 100 (FIG. 4a), or from 0 to 92 (FIG. 4b), or from 0 to 80 (FIG. 4c) where only a monochromatic image comprising character information is displayed, and an area exceeding 100 or 92 or 80 (until 255) where a monochromatic image and a color image including the endoscope image are present in mixed fashion.

Accordingly, the image file controller 3 can recognize the screen composition of the endoscope device 2I being connected at the present based on the device discriminating information inputted thereto, and the image processing section 34 can perform the image processing by using the recognized screen composition information. Stated otherwise, in course of the image processing, the character information area and the endoscope image area can be separated by using the recognized screen composition information from the image signal in which the character information (inspection information) and the endoscope image information are superimposed, enabling the image processing to be carried out in a manner suitable for each of those areas.

Figure 6:
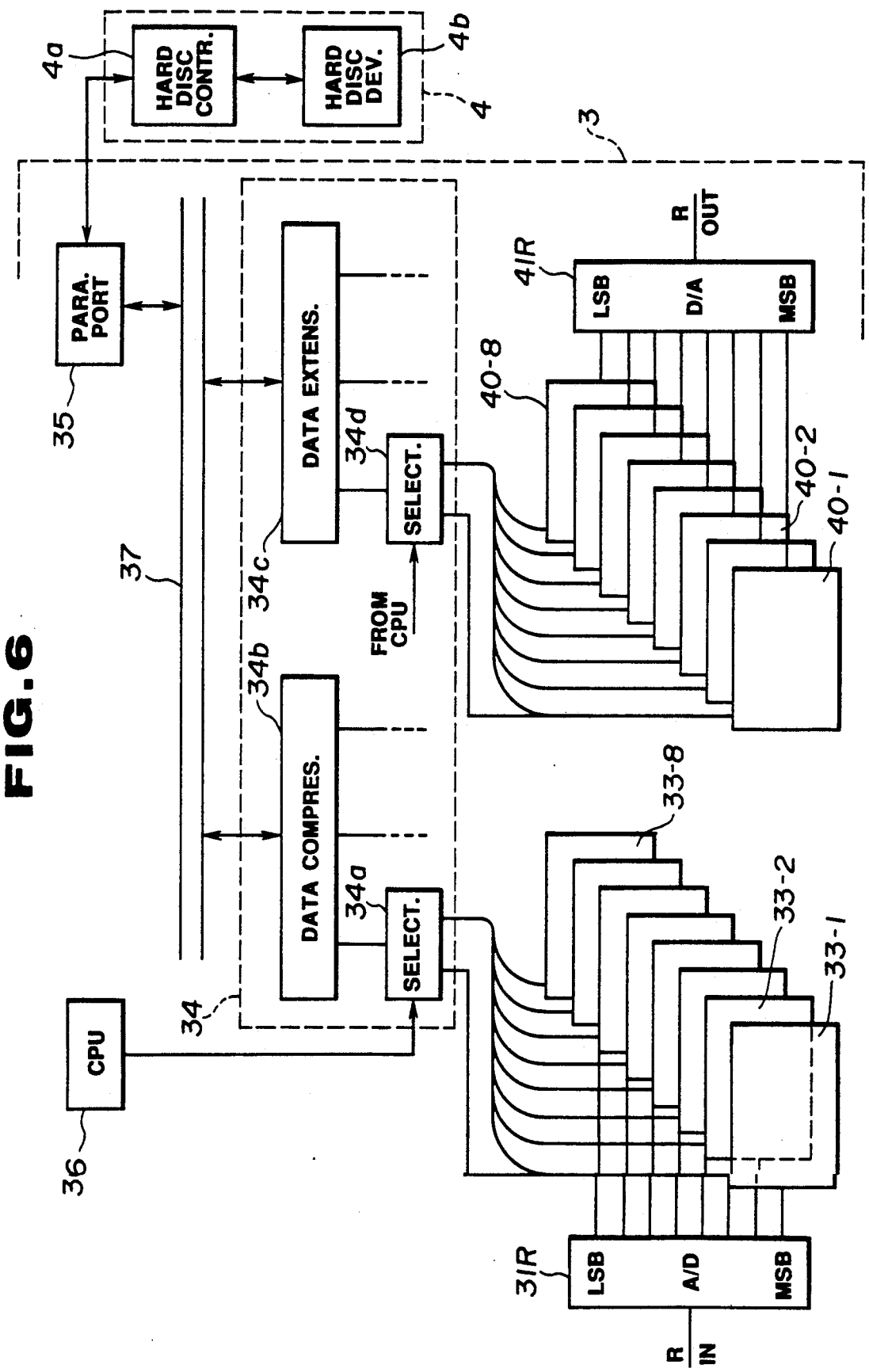

FIG. 6 shows schematic arrangement of the image processing section 34. By way of example, a signal R is recorded in frame memories 33-1, 33-2, . . . , 33-8 via an A/D converter 31R. The frame memories 33-1, 33-2, . . . , 33-8 are connected to a data compression circuit 34b for compression of data via a selector 34a which is switched over by the CPU 36.

Depending on the screen composition information, the selector 34a allows only the data in the most significant frame memory 33-1 to be passed to the data compression circuit 34b for the data in the character information area, but allows all the data in the frame memories 33-1, 33-2, . . . , 33-8 to be passed to the data compression circuit 34b for the data in the endoscope image area. Thus, each pixel data in the character information area is inputted to the data compression circuit 34b in 1-bit code notation for compressing the data. On the other hand, each pixel data in the endoscope image area is inputted to the data compression circuit 34b in 8-bit code notation for compressing the data.

In this embodiment, both the signals for the character information area and the endoscope image area are once converted into digital data by using the common A/D converter 31 and, after the conversion, the image processing section 34 selects the data of each code notation depending on the quantity of information in actual image processing.

Instead of using the common A/D converter 31, it is also possible to provide a comparator in parallel with the A/D converter 31 and a selector for switching over between the A/D converter 31 and the comparator, the selector being operated to select the A/D converter 31 during signal periods of the endoscope image area and the comparator during signal periods of the character information area. In this case, the data binary-coded by the comparator is stored in a memory for 1-bit code notation.

The data having been compressed by the data compression circuit 34b is inputted to the large capacity recording device 4 via the data bus 37 and the parallel port 35, so that the compressed data is recorded in a hard disk device 4b via a hard disk controller 4a, for example, along with information data used in the compression, etc. The hard disk device 4b receives the large capacity recording medium 5 in a removable manner.

Further, a data extension circuit 34c is connected to the data bus 37 and, in a reproduction or retrieval mode, extends the compressed data read out of the had disk device 4b, followed by transfer to frame memories 40-1, 40-2, . . . , 40-8 via a selector 34d. The selector 34d is controlled by the CPU 36 as with the selector 34a.

While FIG. 5 has been explained in connection with the signal R, the above description equally applied to other signals G and B. Additionally, the synch signal S is processed like the signal for the character information area, or recorded and reproduced without being subjected to compression and extension.

Operation of the image processing will be next described.

When the power is turned on, the image file controller 3 requests the image generator 13I for the device discriminating information from the serial port 32 via the cable 24. The image generator 13I sends the device discriminating information to the serial port 32 of the image file controller 3 via the cable 24. The CPU 36 discriminates the type of the endoscope device 2I based on the device discriminating information and transfers the information of screen composition depending on the discriminated type among the set of screen composition information 39b stored in the ROM 39.

As shown in FIG. 4a, for example, the screen composition information stands for such a screen composition that given the total horizontal size of the image data being 255, only a monochromatic image is displayed in the area until 100, and a monochromatic image and a color image are displayed in mixed fashion in the area exceeding 100.

When recording the endoscope image, the image processing section 34 having received the image composition information compresses the data at a compression rate or in a compression manner suitable for each area, by way of example, such that the data in the area until 100 in the horizontal direction is compressed with a binary value to produce a monochromatic image, and the data in the area ranging from 100 to 255 in the horizontal direction is compressed with a multiple value to produce a color image. The compressed image data is sent along with the screen composition information to the large capacity recording device 4 from the parallel port 35 via the cable 25 to be stored in the large capacity recording medium 5.

When reproducing the endoscope image, the image processing section 34 reads the compressed image data, along with the screen composition information, out of the large capacity recording device 4 via the cable 25 and the parallel port 35, performs processing of image data extension depending on the screen composition to restore the data in each area, and further stored the restored display data in the second frame memory 40. The data in the frame memory 40 is inputted to the D/A converter 41 for conversion into the analog video signal of RGB, the video signal being sent to the TV monitor 6 via the cable 26 to display the character information and the endoscope image.

With the above first embodiment, since an image to be processed can be compressed on the basis of screen composition information in a manner suitable for each screen area depending on the screen composition, the image data compression can be efficiently performed, thus enabling reduction in both the amount of data after the compression and a period of time necessary for the processing.

Figure 7:
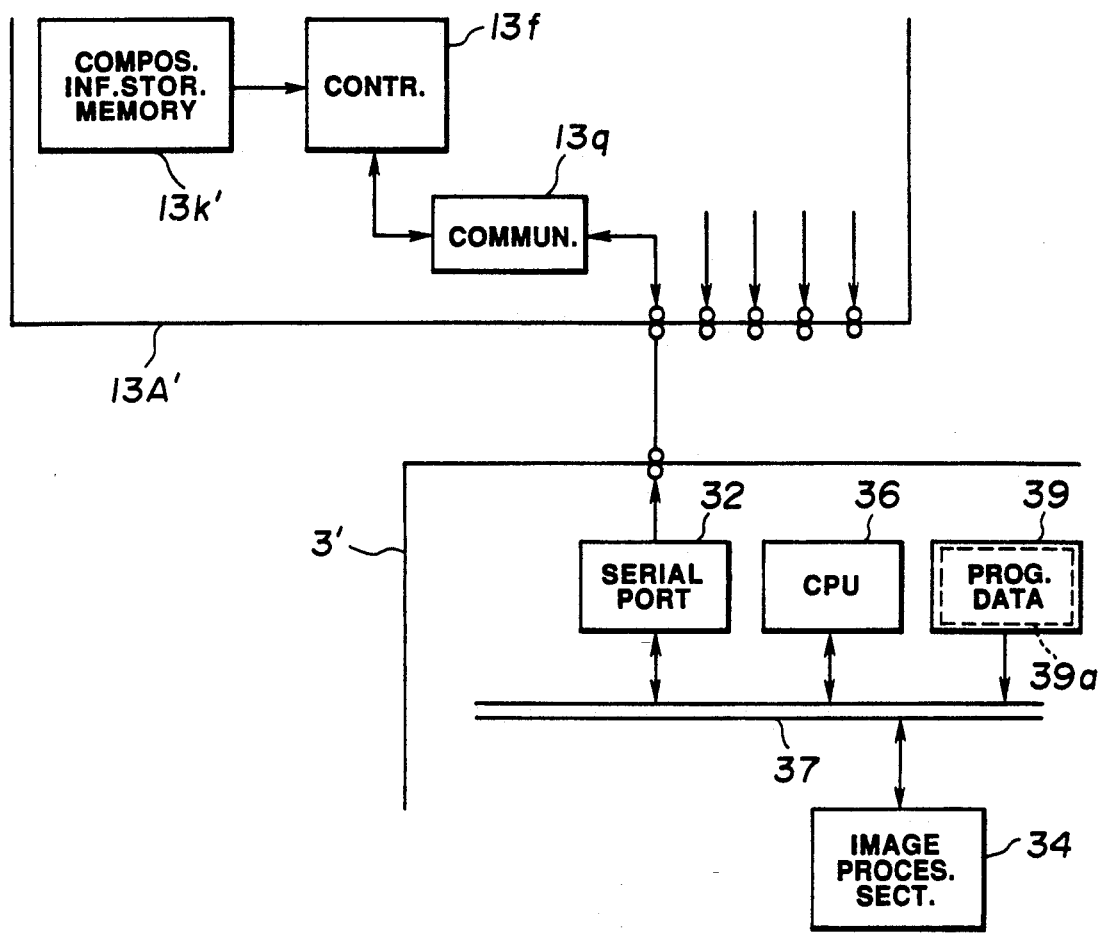

FIG. 7 shows main parts according to a first modification of the first embodiment. An image generator 13A' in this modification has, instead of the memory 13k in FIG. 2 for storing the device discriminating information, a composition information storage memory 13k' which stores the screen composition information indicating the position of the boundary line 45 shown in FIG. 4. The controller 13f transmits the screen composition information to an image file controller 3' via the communication circuit 13q.

The CPU 36 in the image file controller 3' uses the screen composition information transferred via the serial port 32 to control the image processing in the image processing section 34. In this modification, the ROM 39 includes only the program data 39a and requires no storage area for the screen composition information. The remaining arrangement is similar to that in the first embodiment.

With this modification, the image file controller 3' is able to know the composition of two screen areas directly based on the screen composition information received from the image file controller 3' without referring to other information. The remaining operation is similar to that in the first embodiment.

Figure 8:
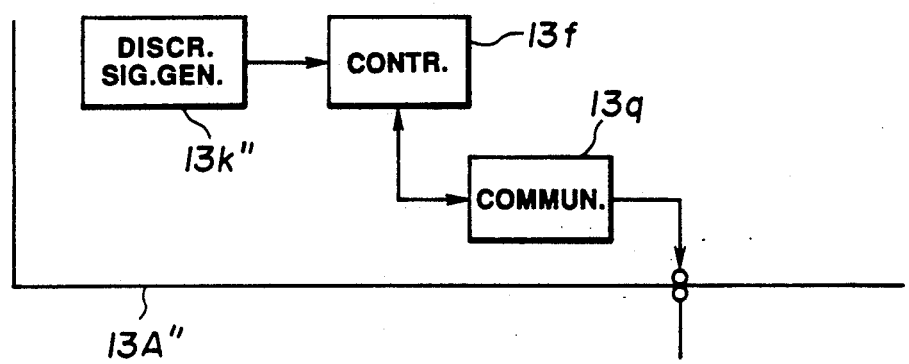

FIG. 8 shows main parts according to a second modification of the first embodiment. An image generator 13A" in this second modification has a discrimination signal generator 13k" instead of the composition information storage memory 13k' in FIG. 7.

The discrimination signal generator 13k" outputs a discrimination signal for discriminating between the endoscope image period and the character information period in the video signal.

In synchronism with the video signal comprising a character information component and an endoscope image component which are superimposed in an time-sharing manner as shown in FIG. 9a, the discrimination signal generator 13k" transmits the discrimination signal (masking signal) shown in FIG. 9c to the image file controller 3' via the communication circuit 13q (from the image generator 13"). The discrimination signal takes a level of "H" during the time the video signal is in a signal period SP for the endoscope image, and a level of "L" during the time it is in a signal period for the character information.

Accordingly, by judging whether the received discrimination signal is at a level of "H" or "L", the CPU 36 can discriminate whether the endoscope image is being transmitted or the character information is being transmitted.

Figure 10:
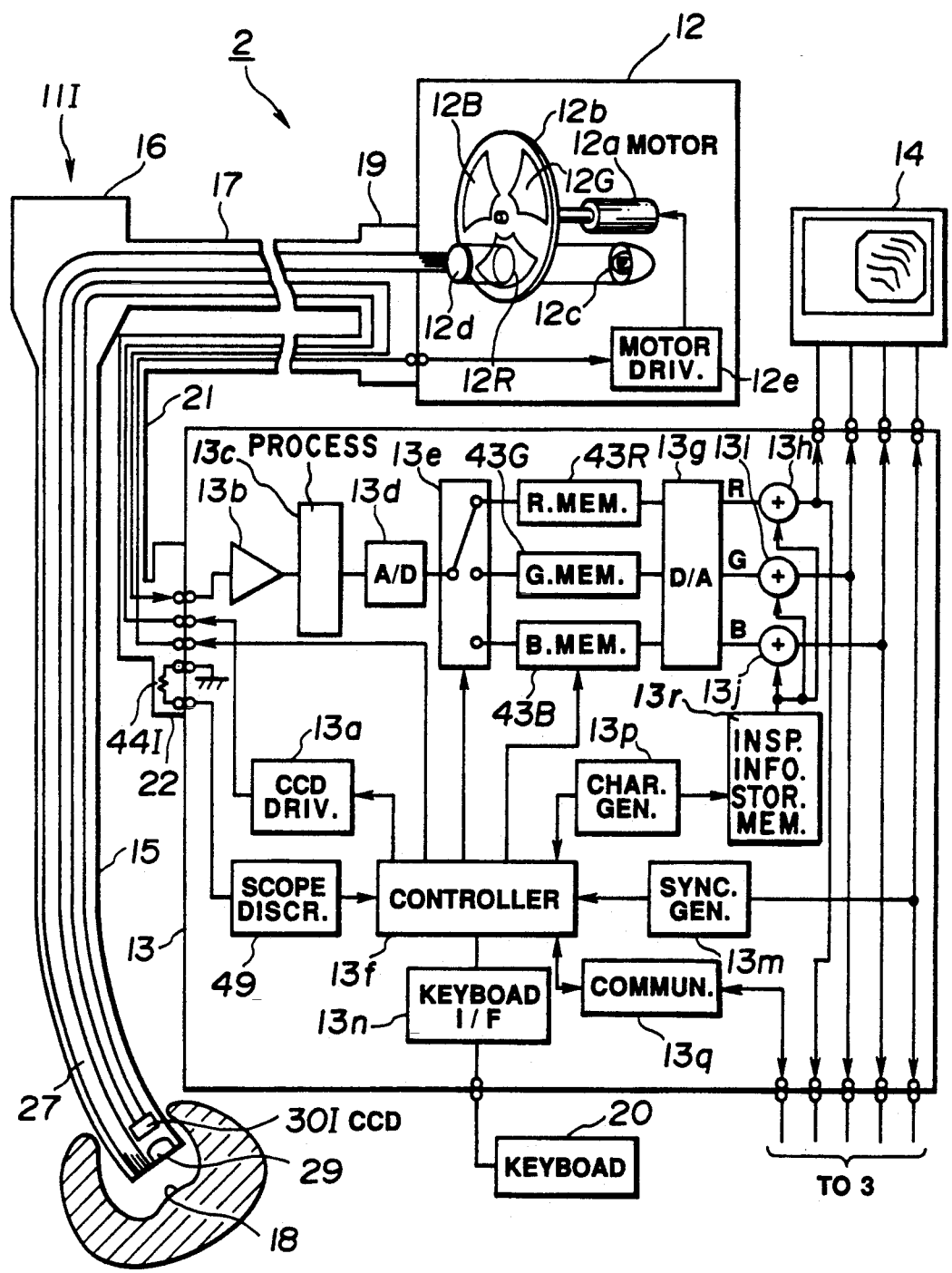

FIG. 10 shows an endoscope device 2 according to a second embodiment of the present invention.

In the first embodiment, various types of different endoscope devices 2A, 2B, etc. are connectable to the image file controller 3. These endoscope devices 2I share one type of the CCD or the electronic scope 11I and the corresponding image generator 13I.

Meanwhile, in the second embodiment, different types of CCDs or electronic scopes 11I can be used by a common image generator 13. Therefore, the image generator 13 in this embodiment additionally includes means for discriminating the type of the electronic scope 11I actually connected thereto. For example, the connectors 22 of the different electronic scopes 11I have connector pins to which are connected resistors 44I set to different values depending on the types of the CCD 30I built in the electronic scopes 11I.

Correspondingly, the image generator 13 includes a CCD discriminating circuit 49 for detecting the resistance value of the connector pins and discriminating the type of the CCD 30I. The CCD discrimination signal recognized by the CCD discriminating circuit 49 is transmitted to the image file controller 3 via the controller 13f and the communication circuit 13q. In the image file controller 3, the CCD discrimination signal is transferred to the CPU 36 via the serial port 32. The CPU 36 reads the screen composition information corresponding to the CCD discrimination signal out of the ROM 39 and utilizes the same for the image processing in the image processing section 34.

Also, upon receiving the CCD discrimination signal, the controller 13f outputs a control signal to the CCD driver 13a so that the CCD drive 13a outputs a CCD drive signal suitable for driving the discriminated CCD 30I. Thus, the CCD driver 13a outputs a CCD drive signal corresponding to the numbers of pixels of the discriminated CCD 30I in both the vertical and horizontal directions.

Because the display area required for displaying the endoscope image is determined by the CCD discrimination signal, the controller 13f controls the read timing from the R, G and B memories 43R, 43G, 43B such that the endoscope image is displayed on the right side of the horizontally long display area of the monitor 14. This control of the read timing is carried out on the basis of the horizontal and vertical synch signals S from the synch signal generating circuit 13m. The remaining arrangement is similar to the first embodiment shown in FIG. 2.

With the second embodiment, different types of the electronic scopes 11I can be handled by the common the image generator 13.

Figure 9:
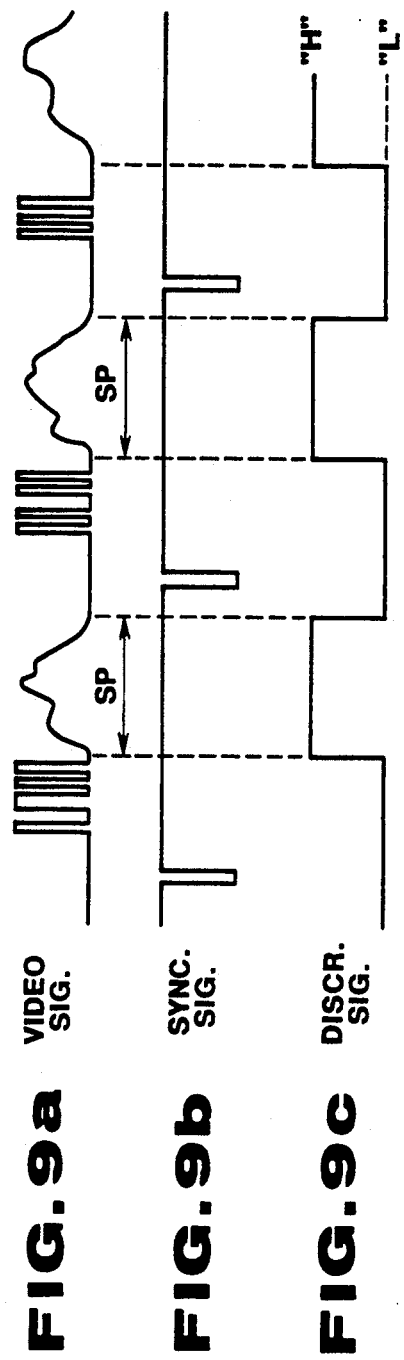
Figure 11:
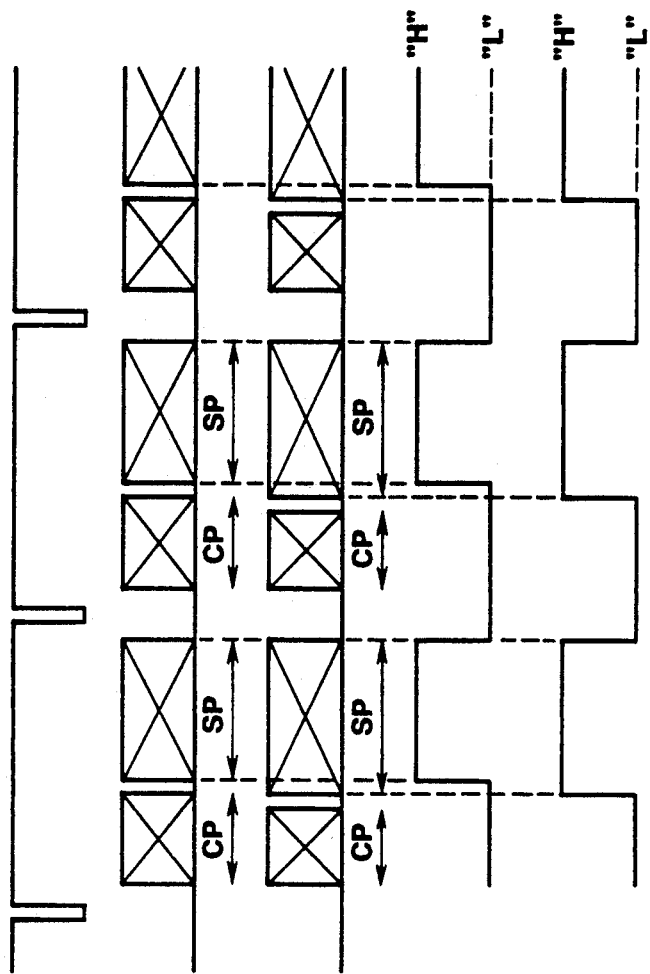

In the above second embodiment, the image generator 13 may transmit the discrimination signal in a manner as explained by referring to FIG. 9 instead of transmitting the CCD discrimination signal to the image file controller 3 as mentioned above. In this case, the discrimination signals transmitted from the image generator 13 to the image file controller 3 depending on two video signals (see FIGS. 11b and 11c) which have different screen compositions because of being different in the number of CCD pixels, for example, are shown in FIGS. 11d and 11e. In FIGS. 11b and 11c, CP stands for a signal period of the character information. FIG. 11a represents the horizontal synch signal.

While the image data is compressed in the above embodiments, the manner of image processing is not limited to the compression and the present invention is also effective in any other type of image processing. Furthermore, the present invention is not limited to the case of the screen composition where the display screen is divided into two areas, it is also applicable to the case of dividing the display screen into three or more areas. Additionally, the manner of dividing the display screen into the character information area and the endoscope image area is not limited to one of dividing it into the two areas in the horizontal direction as illustrated in FIG. 3, but may be practiced by dividing it in the vertical direction as explained later.

Moreover, it is also possible to detect the video signal of RGB, etc. inputted from the image generator 13 to the image file controller 3 through a window comparator or the like on the basis of the horizontal synch signal, for example, and discriminate the character information area or an area which can be regarded equivalent to the character information area, thereby making a judgment that the other area is the endoscope image area. In this case, if the window comparator is so set that its output becomes "0" only during the region between "0" and "1", e.g., the region ranging from 0.25 to 0.75, the comparator output becomes successively "1" at least in the character information area and becomes "1" or "0" in the endoscope image area after the horizontal synch signal. Accordingly, the horizontal signal period which has the shortest period of "1" after the horizontal synch signal can be regarded as the character information area. This case enables the desired processing without needing the discrimination signal for the endoscope device.

Meanwhile, when the endoscope image is displayed as shown in FIG. 4, the distance between the distal end of the electronic scope 11 and the location 18 to be observed is changed depending on the condition of use, the image size of the observed location 18 displayed on the monitor 14 or the like is variable even in the case of using the same endoscope device 2A. The image read out of the large capacity recording device 4 is also similarly variable.

Therefore, difficulties are encountered in comparing images of the same location under observation, for example, with high accuracy. In view of the above, the present invention may be arranged such that the aforesaid distance is calculated by using a stereo type endoscope device of a third embodiment described later, the size of the displayed endoscope image is enlarged/reduced by using the calculated distance, and the images of the same location under observation are displayed in the same size regardless of the different distances.

Figure 12:
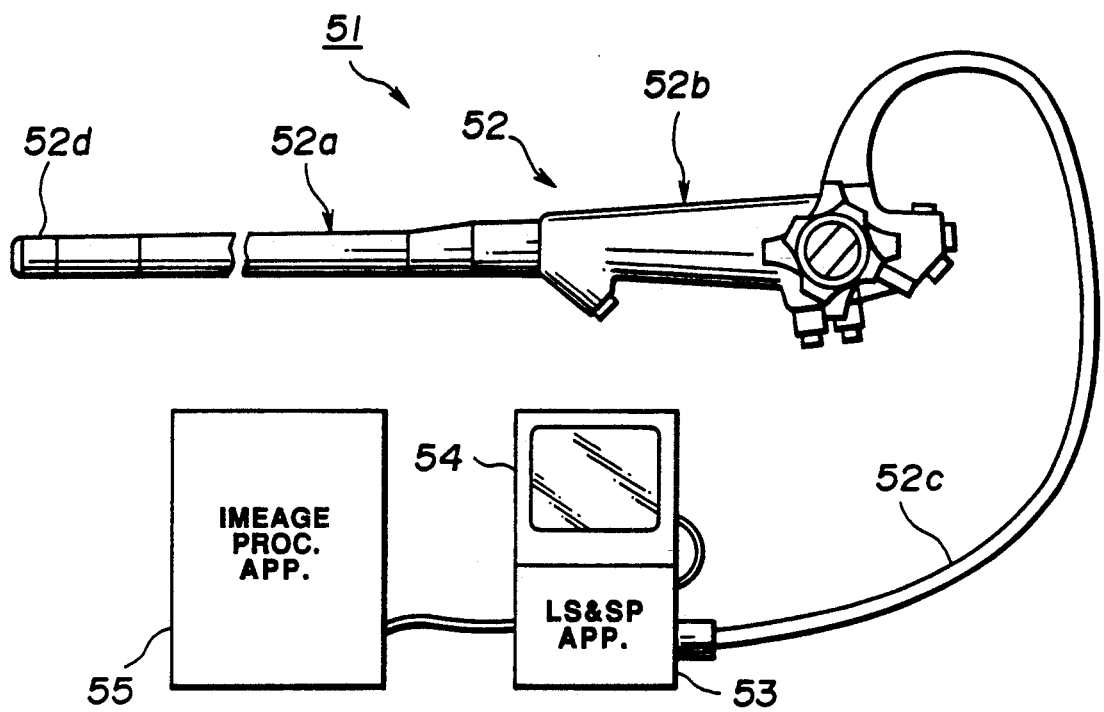

A stereo type endoscope device 51 of a third embodiment shown in FIG. 12 comprises a stereo type endoscope 52 having a pair of image sensing means built therein, a light source and signal processing apparatus 53 having a light source unit and signal processing means built therein to supply an illumination light to illumination light transmitting means of the stereo type endoscope 52, a monitor 54 for displaying a video signal outputted from the light source and signal processing apparatus 53, and an image processing unit or apparatus 55 connected to the light source and signal processing apparatus 53 via a cable to perform image processing for enlarging/reducing the size of two endoscope images.

Figure 13:
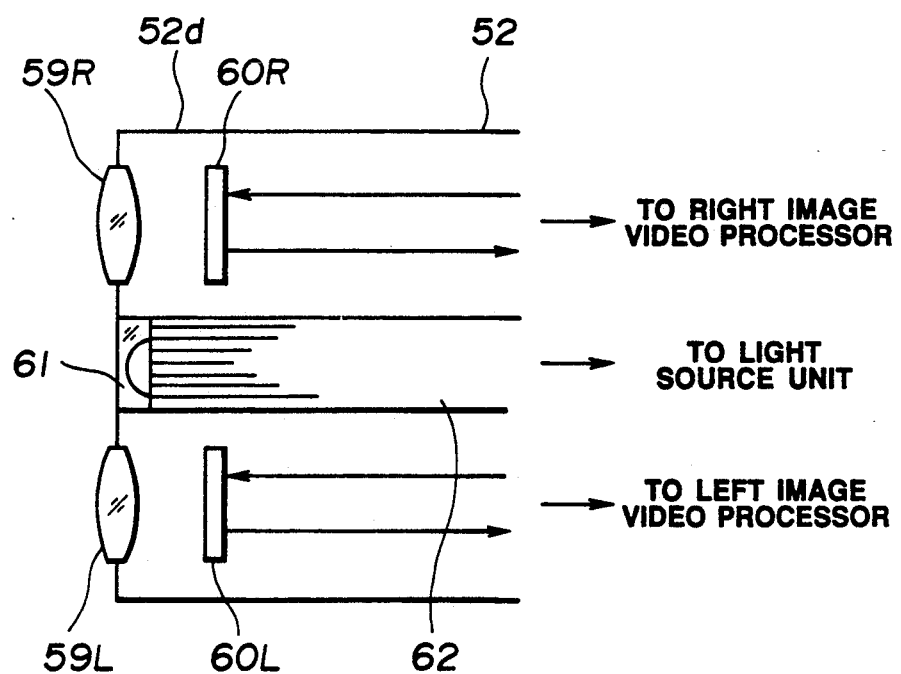

The stereo type endoscope 52 is comprised of an elongate insert section 52a, an operating section 52b formed at the rear end of the insert section 15, and a universal cable 52c extending from the side of the operating section 52b. The insert section 52a has its distal end portion 52d constructed as shown in FIG. 13.

The distal end portion 52d is provided with two observation windows and one illumination window, for example. Inside the observation windows, there are respectively provided a right-eye object lens system 59R and a left-eye object lens system 59R at such positions as producing a parallax. Solid state image sensors 60R, 60L are disposed at the respective focus positions of the object lens systems 59R, 59L. Also, a light directing lens 61 is provided inside the illumination window.

Figure 14:
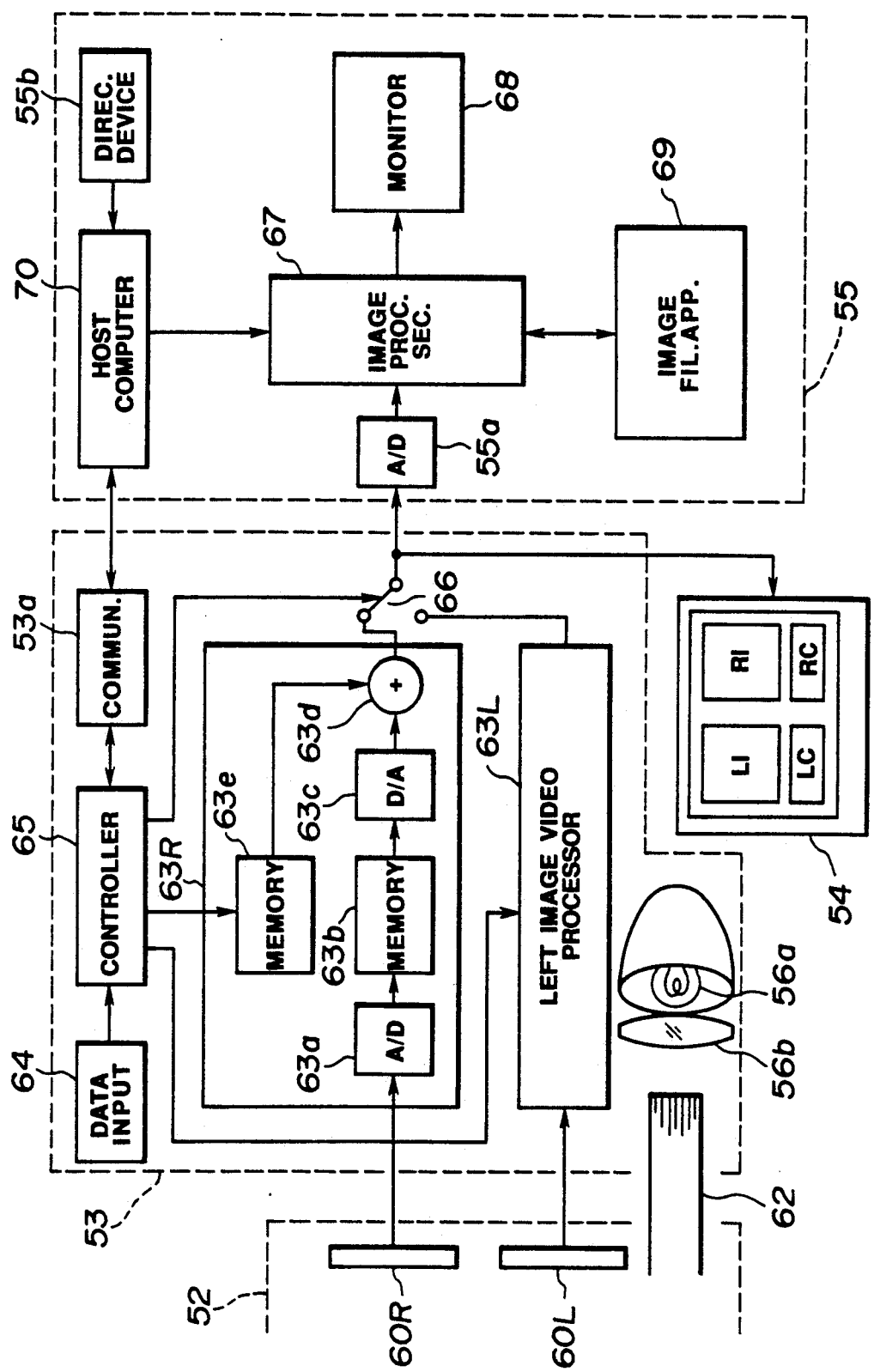

The distal end of a light guide 62 in the form of a fiber bundle is disposed facing the rear end of the light directing lens 61, the rear end of the light guide 62 being connected to a light source unit 56 in the light source and signal processing apparatus 53, shown in FIG. 14, via the insert section 52a and the universal cable 52c.

A white illumination light emitted from a lamp 56a in the light source unit 56 is condensed by a condenser lens 56b to be supplied to the rear end face of the light guide 62. The illumination light is transmitted through the light guide 62 and irradiated toward an object to be sensed, locating in the front, from the distal end face of the light guide 62 through the light directing lens 61.

The light reflected by the object is focused by the object lens systems 59R, 59L on the solid state image sensors 60R, 60L to respectively produce a right image and a left image which are photoelectrically converted into image signals.

The respective image signals are inputted to right image and left image video processors 63R, 63L in the apparatus 53, as shown in FIG. 14, from which video signals are outputted after image processing. For example, the image signal of the solid state sensor 60R is converted into a digital signal by an A/D converter 63a and then temporarily stored in an image memory 63b. The image data stored in the image memory 63b is converted into an analog signal by a D/A converter 63c and, thereafter, superimposed in a mixer 63d on character information from a character information storage memory 63e.

By manually entering data such as an ID code through a data input device 64, the character information is stored in the character information storage memory 63e via a controller 65.

The image signal from the other solid state image sensor 60L is processed by the left image video processor 63L similarly to the above. The two video signals produced by the right image and left image video processors 63R, 63L are mixed by a switch 66 into one video signal in a time-sharing manner, following which the mixed video signal is outputted along with synch signals (not shown) to a monitor 54 and the image processing unit 55. The monitor 54 displays not only two endoscope images, LI, RI separated in the horizontal direction, but also character images LC, RC vertically (downwardly as shown) separated from the endoscope images LI, RI.

The video signal is converted into a digital signal by an A/D converter 55a and then inputted to an image processing section 67. The image processing section 67 performs processing to measure the distance between the distal end of the endoscope and the location under observation, as well as processing to enlarge/reduce an image based on the measured result. After the processing for enlargement/reduction, the video signal is displayed on the monitor 68.

An image file apparatus 69 is connected to the image processing section 67 to carry out recording and reproduction of images with respect to a recording medium.

A host computer 70 controls the image processing section 67 and makes computations to measure the distance between the distal end of the endoscope and the location under observation. The host computer 70 is connected to an instruction or directive device 55b such as a keyboard or mouse, allowing the operator to enter information necessary for retrieval or instruct the point to be measured.

Further, the host computer 70 is connected to the light source and signal processing apparatus 53 via a communication circuit 53a so that screen composition information for the video signal (which is inputted from the light source and signal processing apparatus 53 to the image processing unit 55) is transmitted to the host computer 70 from the controller 65 in the light source and signal processing apparatus 53.

Figure 16:
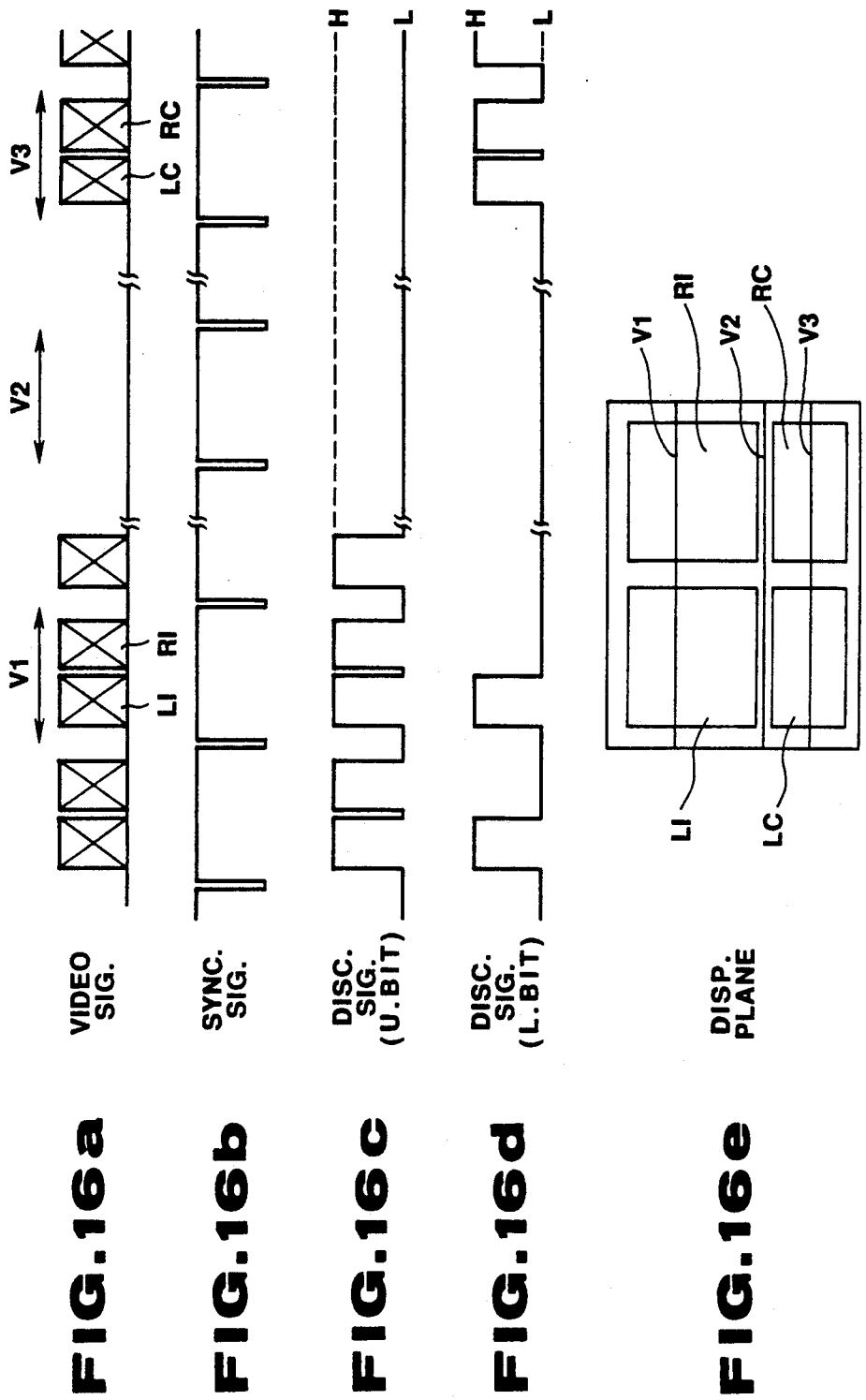

The screen composition information comprises 2-bit discrimination signals as shown in FIGS. 16c and 16d, for example, in synchronism with the video signal shown in FIG. 16a. Periods of the video signal indicated by V1, V2, V3 in FIG. 16a correspond to scan lines V1, V2, V3 on the display screen of FIG. 16e, respectively. As shown in FIG. 16e, the display screen of the monitor 54 is divided such that the left image LI and the right image RI are displayed in areas separated in the horizontal direction, while the inspection information LC and RC associated with the respective images are displayed in areas separated from each other in the horizontal direction and also downwardly of the areas for the left image and the right image in the vertical direction. Thus, V2 becomes a line dividing the endoscope images and the inspection information in the vertical direction.

As shown in FIG. 6c, for example, the upper bit of the discrimination signal takes a level of "H" during signal periods of the endoscope image and a level of "L" during signal periods of the inspection information. On the other hand, the lower bit of the discrimination signal takes a level of "H" during signal periods of the inspection information. During signal periods of the inspection information, the lower bit takes a level of "H" during signal periods of the left image and a level of "L" during signal periods of the right image, for example.

The host computer 70 transfers the above 2-bit discrimination signal to the image processing section 67 so that the image processing is carried out on only the endoscope images.

Figure 15:
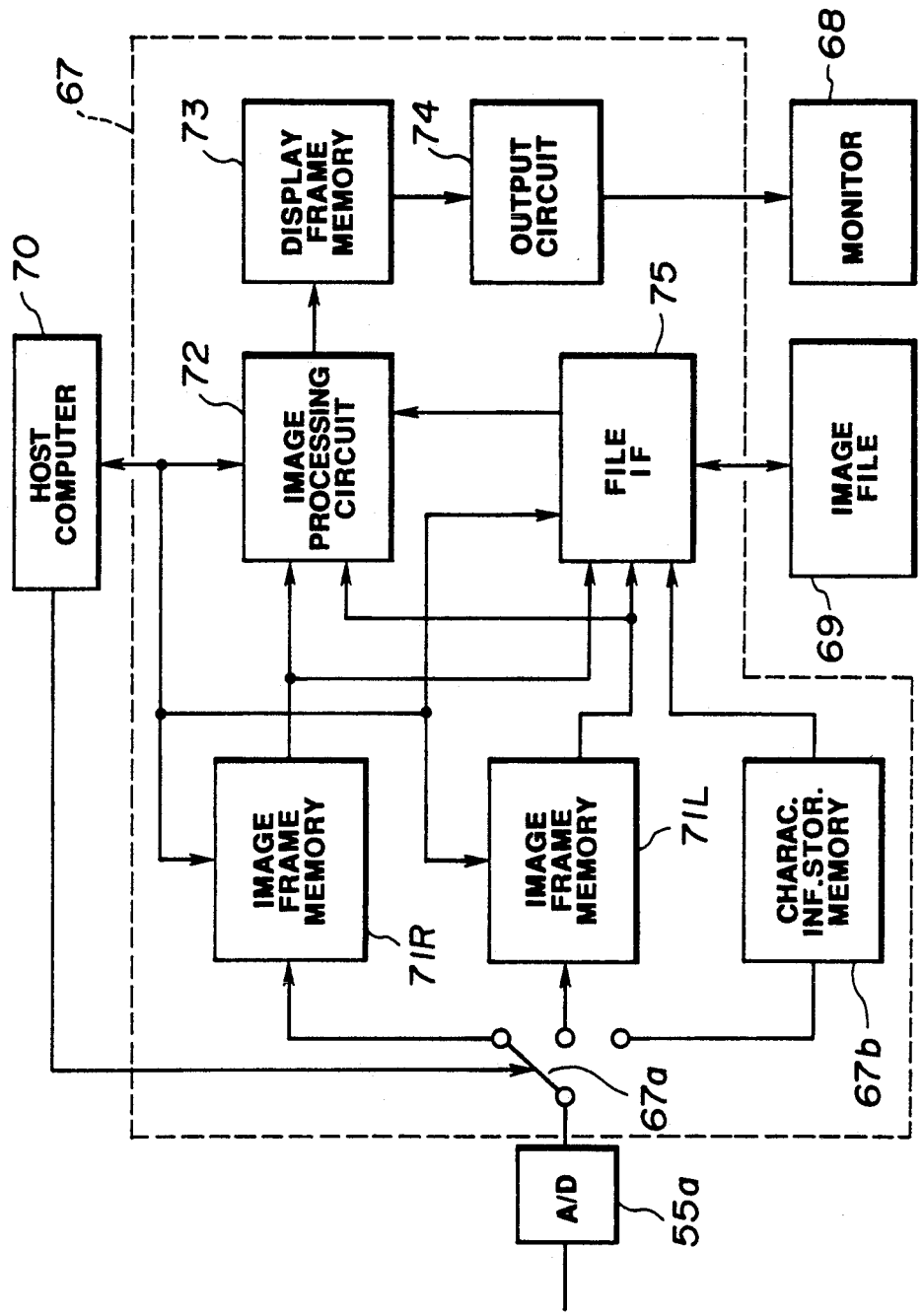

FIG. 15 shows arrangement of the image processing section 67.

In the image processing section 67, the A/D-converted video data is separated into threes by a selector 67a which is changed over under control of a switching signal in the form of the 2-bit discrimination signal transferred from the host computer 70, the separated three data being temporarily stored in image frame memories 71R, 71L and the character information storage memory 67b. Specifically, the image sensed by the solid state image sensor 60R is stored in the frame memory 71R, the image sensed by the solid state image sensor 60L is stored in the frame memory 71L, and the character information is stored in the character information storage memory 67b.

The video signal data in the frame memories 71R and 71L enable the monitor 68 to simultaneously display two images in superimposed relation through an image processing circuit 72, a display frame memory 73 and an output circuit 74, and also enable computations to determine the distance until the point to be measured by the host computer 70.

The distance information determined by such computations is outputted to the image processing circuit 72 which carries out a magnification varying process based on the distance information so that the image displayed on the monitor 62 may be displayed at varying magnification.

The images stored in the image frame memories 71R, 71L as well as the character information stored in the character information storage memory 67b can be recorded in the image file apparatus 69 via an file interface 75 along with the distance information. Further, when retrieving an image from the image file apparatus 69, the retrieved image can be displayed on the monitor 68 via the file interface 75, the image processing circuit 72, the display frame memory 73 and the output circuit 74.

In an attempt of displaying one image reproduced from the image file apparatus 69 and one image from the stereo type endoscope 52 on the monitor 68 at the same time, both the images can be displayed at the same size by varying magnification of the image from the endoscope 52 using the associated distance information and varying magnification of the image from the image file apparatus 69 using the distance information obtained at the time of sensing the image.

Figure 17:
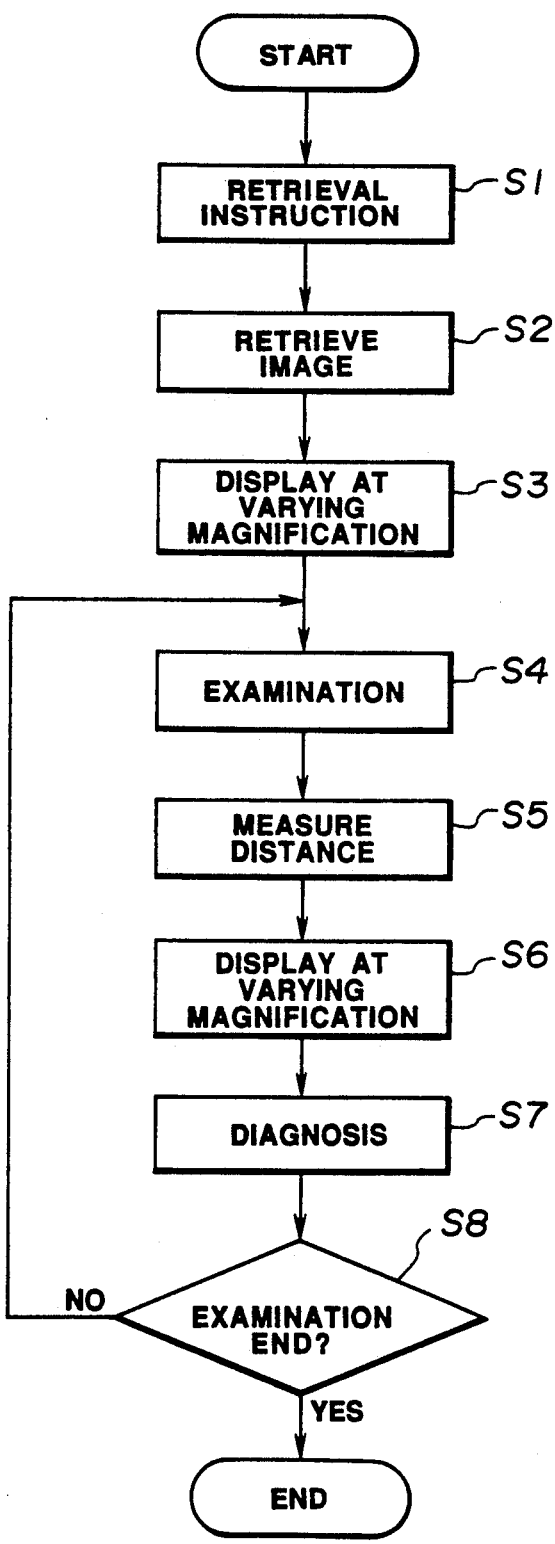

FIG. 17 shows one example of an examination or inspection flow and FIG. 18 shows examples of monitor images displayed through the examination flow.

Figure 18A:
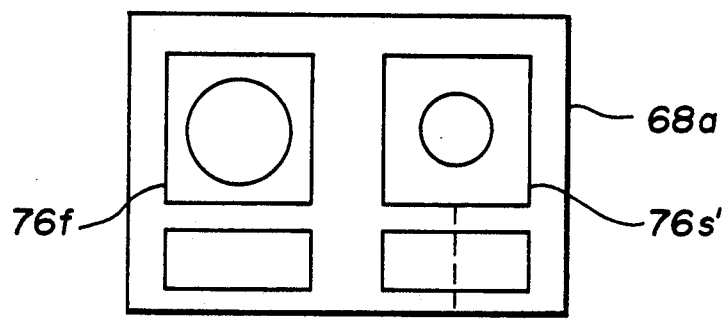
Figure 18B:
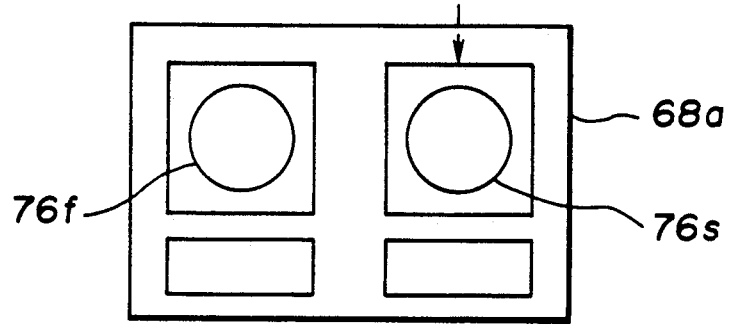

When the examination flow starts up, information necessary for retrieval is first inputted from the instruction device 55b in a step S1. Then, an image is retrieved from the image file apparatus 69 based on the inputted retrieval information in a step S2. Simultaneously, the distance information between the distal end of the endoscope and the location under observation obtained at the time of sensing the image is also read out of the image file apparatus 69 and the read-out information is used to perform the magnification varying process for changing the size of the displayed image (step S3). At this time, the image data retrieved from the image file apparatus 69 causes the monitor 68 to display a retrieved image 76f on the left side in a monitor screen 68a as shown in FIG. 18a or 18b, for example, via the file interface 75, the image processing circuit 72, the display frame memory 73 and the output circuit 74.

It is now assumed that an endoscope examination is to be performed as indicated in a step S4. Upon reaching the location to be observed, like the diseased part, the instruction device 55b is operated to instruct the host computer 70 to carry out a process of computations for measuring the distance based on the information such as the difference in output between the two solid state image sensors 60R and 60L (step S5). On this occasion, the operator may instruct the corresponding position of the location to be observed by displaying the two images from the stereo type endoscope 52 on the monitor 68 alternately or simultaneously.

Next, the input image is displayed while being varied in magnification or size based on the measured result (step S6). At this time, the input image is stored in the image frame memory 71R (or 71L) from the stereo type endoscope 52 via the video processor 63R (or 63L), and the image in either one image frame memory 71R (or 71L), which is set in advance, is displayed as an examination image 76s on the monitor screen 68a at the right of the file image 76f, as shown in FIG. 18b, via the image processing circuit 72, the display frame memory 73 and the output circuit 74.

Here, the two images 76f, 76s represent the location to be observed at the same size. Accordingly, the operator can make a diagnosis, as indicated in a step S7, by viewing the two images 76f, 76s for comparison. After the diagnosis, the process of examination to diagnosis in the steps S4–S7 will be repeated by responding NO in a step S8 which prompts a judgment as to whether or not to end the examination. Upon responding YES in the judgment of the step S8, the examination flow is brought into an end.

Figures 19A, 19B:
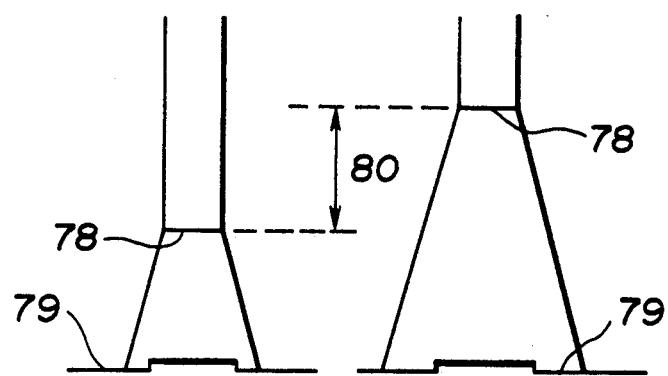

FIG. 19 is a set of explanatory views relating to the distance between a distal end face 78 of the endoscope 52 and a location 79 to be observed. Assuming that the image sensed under the condition of FIG. 19a is displayed as 76f in FIG. 18a, the image sensed under the condition of FIG. 19b is displayed as 76s' in FIG. 18a at the relatively small size. By performing the magnification varying process (e.g., the enlarging process in this case) depending on a difference 80 between the distances by which the respective images are sensed, the image sensed under the condition of FIG. 19b can be displayed as 76s in FIG. 18b at the same relative size.

Additionally, the data recorded in the image file apparatus 69 includes the image data and the distance information at the time of sensing the image in the same recording unit. With the endoscope device 51 of this embodiment, the image obtained during the past examination and the image obtained during the current examination can be both displayed in the endoscopic examination, enabling the operator to easily observe changes of the same location to be observed over time including the size.

While the above stereo type endoscope 52 is always provided with two image sensing systems in the distal end portion 58, the present invention may be arranged to permit stereo observation on demand by, as shown in FIG. 20, inserting another image sensing unit 84 of the same characteristics into a channel 83 of an electronic endoscope 82 having one image sensing unit 81 built therein, raising a forceps lift stand 86 via a forceps lift wire 85 and changing a viewing directing 87 of the image sensing unit 84.

In FIG. 20, the image sensing unit 81 built in the electronic endoscope 82 and the image sensing unit 84 inserted into the channel 83 respectively include object optical systems 88a, 88b and CCDs 89a, 89b disposed on the focal planes of the object lens systems 88a, 88b. Circuit boards are provided on the rear side of the CCDs 89a, 89b to mount electronic parts thereon with signal cables 90a, 90b connected to the respective circuit boards. In this electronic endoscope 82, the viewing direction 87 of the image sensing unit 84 can be changed by the operation of raising the forceps lift stand 86. Accordingly, by carrying out the raising operation depending on the distance up to the object to be observed, the observed object can be set at a position where the viewing direction of the image sensing unit crosses the viewing direction 87 of the image sensing unit 84, and thus can be put at the center of each field of view.

It should be understood that the present invention is not limited to the embodiments and modifications as set forth above, and other embodiments such as constituted by combining parts of the different embodiments with each also belong to the scope of the invention.

What is claimed is:

1. The endoscope image processing system comprising:
   an endoscope having an insert section to be inserted into a body cavity or the like and an image sensor for photoelectrically converting an optical image obtained through an object lens provided at a distal end of said insert section;
   a video signal generating means for generating a video signal which contains an endoscope image produced through signal processing for said image sensor and image information different in quantity of information per unit from said endoscope image;
   information generating means provided in said video signal generating means for automatically generating information corresponding to an area arrangement for respective signal areas of said endoscope image and said image information contained in said video signal; and
   an image processing unit connected to said information generating means via communication means, through which said information is transmitted, for carrying out image processing in different manners for said endoscope image and said image information contained in said video signal based on said information transmitted via said communication means.

2. The endoscope image processing system according to claim 1, wherein said image processing unit carries out image processing by converting said endoscope image and said image information into different quantities of information per unit signal period per unit pixel.

3. The endoscope image processing system according to claim 1, wherein said image processing unit carries out image processing of data compression for said endoscope image and said image information to reduce quantities of information per unit signal period per unit pixel.

4. The endoscope image processing system according to claim 1, wherein said image information is character information containing an ID code to identify said endoscope image.

5. The endoscope image processing system according to claim 1, wherein said endoscope is an electronic scope having said image sensor disposed at the focal plane of said object lens.

6. The endoscope image processing system according to claim 1, wherein said endoscope has a light guide for transmitting an illumination light therethrough and emitting said illumination light from its one end fixed at a distal end of said insert section, and supplying said illumination light to another end face of said light guide.

7. The endoscope image processing system according to claim 1, further comprising a recording device for recording a signal subjected to the image processing in said image processing device.

8. The endoscope image processing system according to claim 1, wherein said information generating means generates information of said area arrangement specific to said video signal generating means.

9. The endoscope image processing system according to claim 1, wherein said information generating means generates, in synchronism with said video signal, a signal having different levels between a signal period of said endoscope image and a signal period of said image information contained in said video signal.

10. The endoscope image processing system according to claim 1, wherein said information generating means generates, as information of said area arrangement, information for dividing said endoscope image and said image information corresponding to the type of said image sensor in said endoscope.

11. The endoscope image processing system according to claim 1, wherein said information generating means has discrimination means for discriminating the type of said image sensor in said endoscope to be connected to said video signal generating means.

12. The endoscope image processing system according to claim 1, wherein said video signal generating means generates a video signal determining screen composition which is different depending on the type of said image sensor in said endoscope to be connected to said video signal generating means.

13. The endoscope image processing system according to claim 1, wherein said information generating means generates discrimination information specific to said video signal generating means.

14. The endoscope image processing system according to claim 13, wherein said information generating means has means for generating reference information and is adapted to recognize said area arrangement by using said discrimination information.

15. The endoscope image processing system according to claim 1, further comprising a monitor to display said video signal on a display screen.

16. The endoscope image processing system according to claim 15, wherein said information generating means generates, as information of said area arrangement, information for dividing said endoscope image and said image information both displayed on a display screen of said monitor.

17. The endoscope image processing system according to claim 16, wherein said information generating means generates position information for dividing said endoscope image and said image information, both displayed on a display screen of said monitor, at a vertical boundary line.

18. The endoscope image processing system according to claim 16, wherein said information generating means generates information for dividing said endoscope image and said image information to be separately displayed on the display screen of said monitor in the vertical direction.

19. The endoscope image processing system according to claim 1, wherein said endoscope has two image sensors.

20. The endoscope image processing system according to claim 19, wherein said video signal generating means produces a video signal containing two endoscope images sensed by said two image sensors.

21. The endoscope image processing system according to claim 20, wherein said information generating means generates a discrimination signal adapted to discriminate said two endoscope images.

22. The endoscope image processing system according to claim 20, wherein said image processing unit performs image processing to change the image size of one of said two endoscope images.

23. The endoscope image processing system according to claim 20, further comprising a monitor adapted to display said two endoscope images.

24. The endoscope image processing system comprising: an endoscope having an insert section to be inserted into the body cavity or the like and an image sensor for photoelectrically converting an optical image obtained through an object lens provided at the distal end side of said insert section;

a video signal generating means for generating a video signal which contains an endoscope image produced through signal processing for said image sensor and a character image consisted of character information relating to said endoscope image;

information generating means provided in said video signal generating means for automatically generating information corresponding to an area arrangement for respective signal areas of said endoscope image and said image character image, and an image processing unit connected to said information generating means via communication means, through which said information is transmitted, for carrying out image processing in different manners for said endoscope image and said character image contained in said video signal based on said information transmitted via said communication means.

25. The endoscope image processing system comprising:

a video signal generating means for generating a video signal which contains an endoscope image produced through signal processing for a image sensor of an endoscope and a character image consisting of character information relating to said endoscope image;

information generating means provided in said video signal generating means for automatically generating information corresponding to an area arrangement for respective signal areas of said endoscope image and said image character image; and an image processing unit connected to said information generating means via communication means, through which said information is transmitted, for carrying out image processing in different manners for said endoscope image and said character image contained in said video signal based on said information transmitted via said communication means.

* * * * *